(12) United States Patent
Smith

(10) Patent No.: US 8,603,062 B1
(45) Date of Patent: Dec. 10, 2013

(54) FEMININE HYGIENIC PAD ASSEMBLY

(76) Inventor: Sherian A. Smith, Lyman, SC (US)

( * ) Notice: Subject to any disclaimer, the term of this patent is extended or adjusted under 35 U.S.C. 154(b) by 310 days.

(21) Appl. No.: 13/025,346

(22) Filed: Feb. 11, 2011

(51) Int. Cl.
- *A61F 13/15* (2006.01)
- *A61F 13/47* (2006.01)
- *A61F 13/64* (2006.01)

(52) U.S. Cl.
USPC ............................ 604/392; 604/387; 604/393

(58) Field of Classification Search
USPC .......... 604/385.01, 385.15, 385.21, 386, 387, 604/392, 393, 402, 388–391; 2/46, 400, 2/406
See application file for complete search history.

(56) References Cited

U.S. PATENT DOCUMENTS

| | | | |
|---|---|---|---|
| 1,886,642 A | 11/1932 | Castle | |
| 2,272,830 A | 2/1942 | Brody et al. | |
| 2,408,723 A | 10/1946 | Arpin et al. | |
| 2,839,057 A | 6/1958 | Argyll | |
| 2,928,394 A * | 3/1960 | Roberts | 604/397 |
| 3,038,474 A | 6/1962 | Harwood et al. | |
| 4,905,323 A | 3/1990 | Lampman | |
| 5,325,543 A | 7/1994 | Allen | |
| 5,733,275 A * | 3/1998 | Davis et al. | 604/387 |
| 5,870,778 A * | 2/1999 | Tharpe | 2/400 |
| D445,181 S | 7/2001 | Kramer | |
| 6,632,210 B1 * | 10/2003 | Glasgow et al. | 604/385.17 |
| 6,772,446 B1 | 8/2004 | Black | |
| 7,125,401 B2 * | 10/2006 | Yoshimasa | 604/392 |
| 2002/0035747 A1 | 3/2002 | Kusibojoska et al. | |
| 2003/0114812 A1 * | 6/2003 | Braverman et al. | 604/367 |
| 2005/0209577 A1 * | 9/2005 | Tong | 604/387 |

OTHER PUBLICATIONS

The American Heritage® Dictionary of the English Language, Fourth Edition copyright ©2000 by Houghton Mifflin Company definition of circular.*

* cited by examiner

*Primary Examiner* — Lynne Anderson
*Assistant Examiner* — Kathryn E Ditmer

(57) ABSTRACT

A feminine hygienic pad assembly includes a panel that is configured to absorb and retain fluids. The panel includes a first end section, a second end section and a central section extending between the first and second end sections. The first and second end sections have a circular shape, and the first and second lateral edges of the central section are concavely arcuate. A base member is flexible and has an inner surface and an outer surface. The panel is attached to the inner surface. The base member has a first edge and a second edge positioned opposite of each other. First and second straps each extend between the first and second edges of the base member. The first and second straps are positioned on opposite sides of the base member.

9 Claims, 5 Drawing Sheets

FEMININE HYGIENIC PAD ASSEMBLY

BACKGROUND OF THE DISCLOSURE

Field of the Disclosure

The disclosure relates to feminine sanitary pad devices and more particularly pertains to a new feminine sanitary pad device for preventing menstrual leakage.

SUMMARY OF THE DISCLOSURE

An embodiment of the disclosure meets the needs presented above by generally comprising a panel that is configured to absorb and retain fluids. The panel has a first end, a second end, a first lateral edge and a second lateral edge. The panel includes a first end section including the first end, a second end section including the second end and a central section that is attached to and extends between the first and second end sections. Each of the first and second end sections has a circular shape, while the first and second lateral edges of the central section are concavely arcuate. A base member is flexible and has an inner surface and an outer surface. The panel is non-removably attached to the inner surface. The base member has a first edge and a second edge positioned opposite of each other. A first strap has a first end attached to the base member adjacent to the first edge and a second end to the base member adjacent to the second edge. A second strap has a first end attached to the base member adjacent to the first edge and a second end to the base member adjacent to the second edge. The first and second straps are positioned on opposite sides of the base member.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
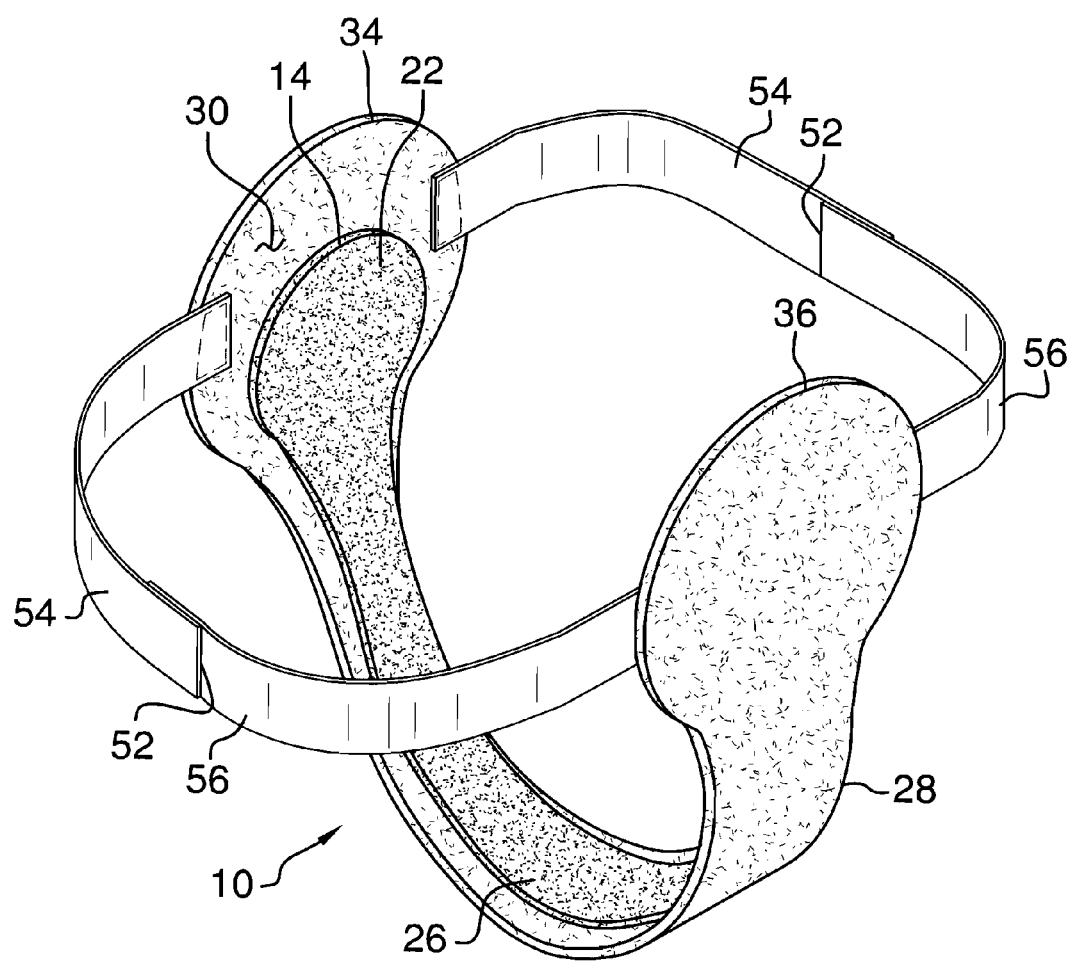
FIG. 1 is a top perspective view of a feminine hygienic pad assembly according to an embodiment of the disclosure.
Figure 2:
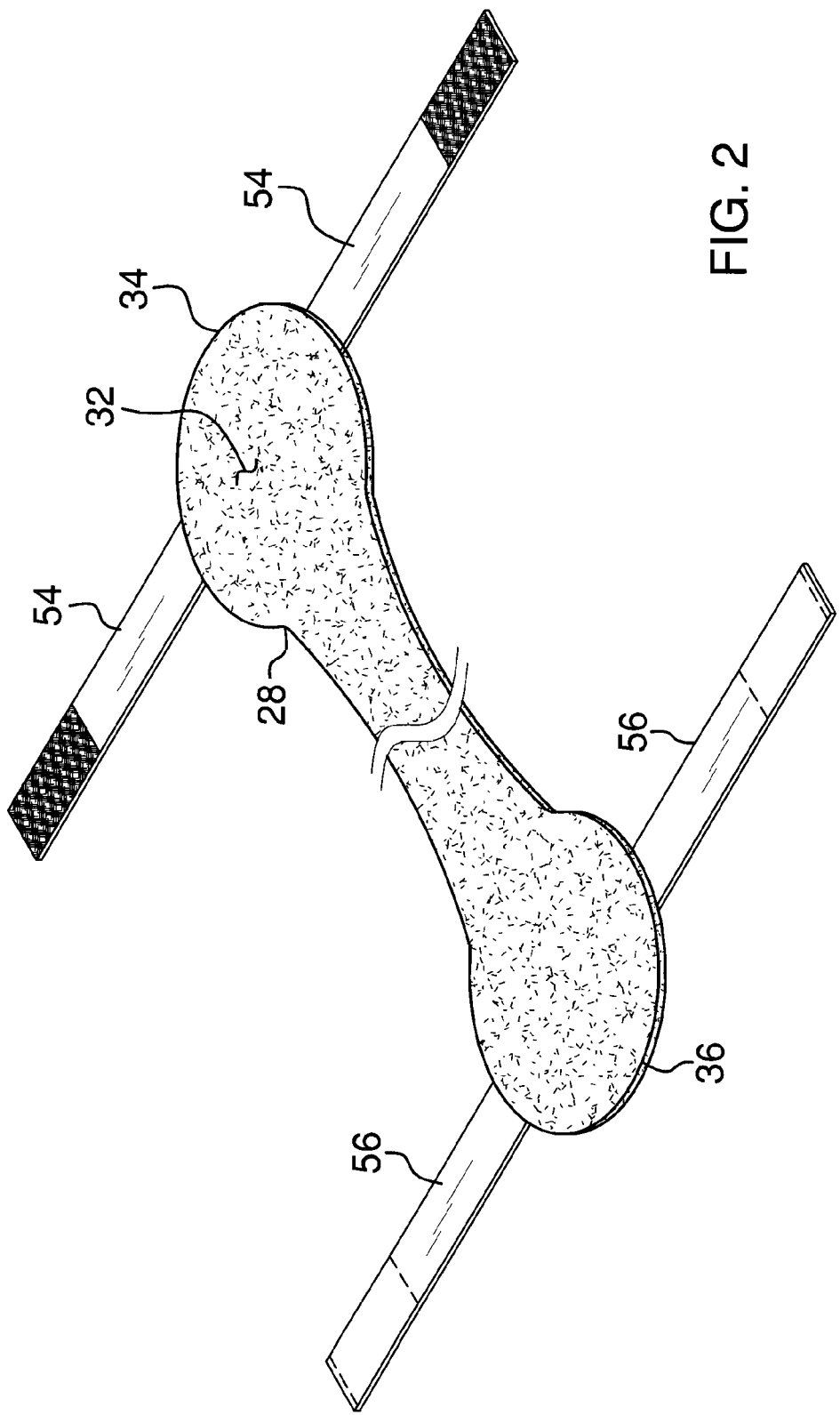
FIG. 2 is a bottom perspective view of an embodiment of the disclosure.
Figure 3:
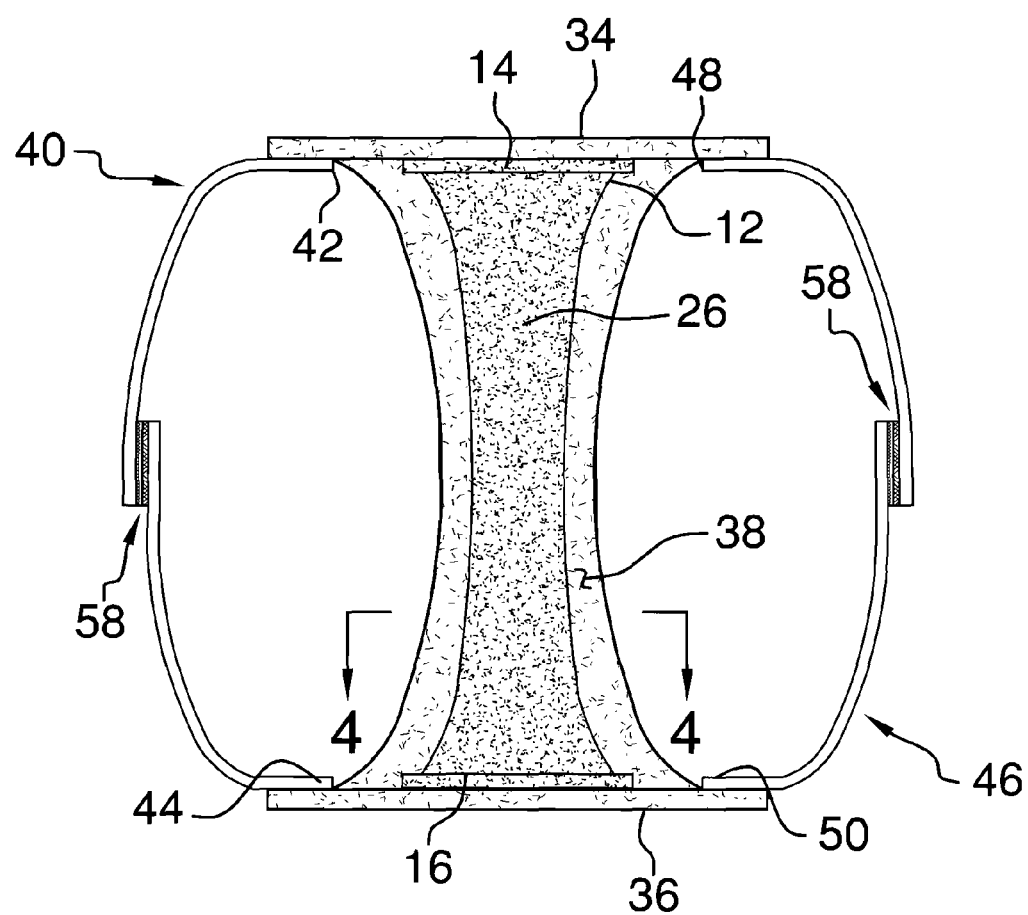
FIG. 3 is a top view of an embodiment of the disclosure.
Figure 4:
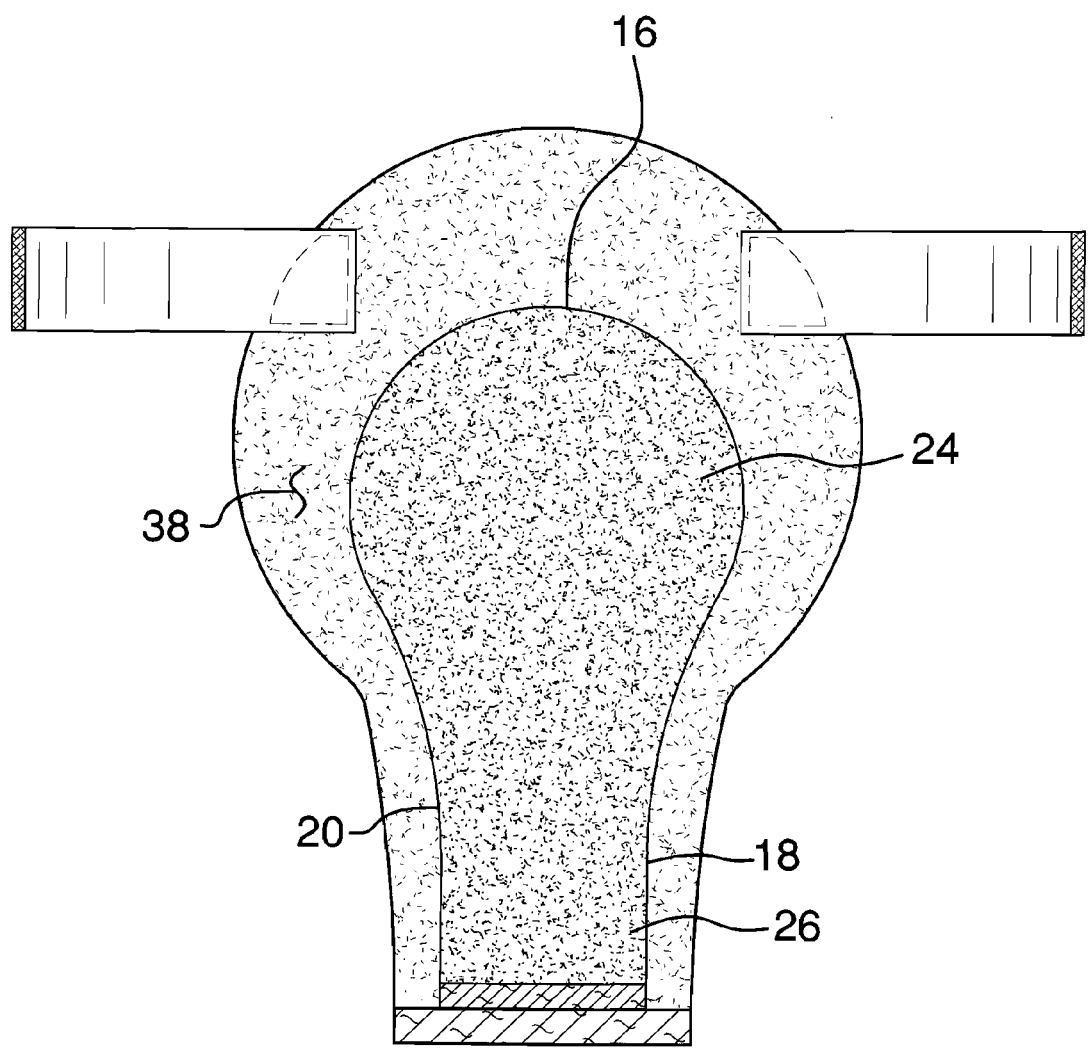
FIG. 4 is a cross-sectional view of an embodiment of the disclosure taken along line 4-4 of FIG. 3.

With reference now to the drawings, and in particular to FIGS. 1 through 5 thereof, a new feminine sanitary pad device embodying the principles and concepts of an embodiment of the disclosure and generally designated by the reference numeral 10 will be described.

As best illustrated in FIGS. 1 through 5, the feminine hygienic pad assembly 10 generally comprises a panel 12 that is configured to absorb and retain fluids. The panel 12 has a first end 14, a second end 16, a first lateral edge 18 and a second lateral edge 20. The panel 12 has a first end section 22 including the first end 14, a second end section 24 including the second end 16 and a central section 26 that is attached to and extends between the first 22 and second 24 end sections. Each of the first 22 and second 24 end sections has a circular shape The first 18 and second 20 lateral edges of the central section 26 may be concavely arcuate. The panel 12 has a length from the first end 14 to the second end 16 greater than 20 cm and may have a length greater than 25 cm to ensure adequate coverage. The first 22 and second 24 end sections each have a greatest width being greater than 10 cm.

A base member 28 is flexible and has an inner surface 30 and an outer surface 32. The panel 12 is non-removably attached to the inner surface 30 and the base member 28 has a first edge 34 and a second edge 36 positioned opposite of each other. The base member 28 has a size and shape such that a peripheral flange 38 is formed between the base member 28 and the panel 12 and extends completely around the panel 12. In particular the base member 28 has approximately the same shape as the pad 12. The base member 28 is comprised of a cloth material, which may be a synthetic or natural material.

Figure 5:
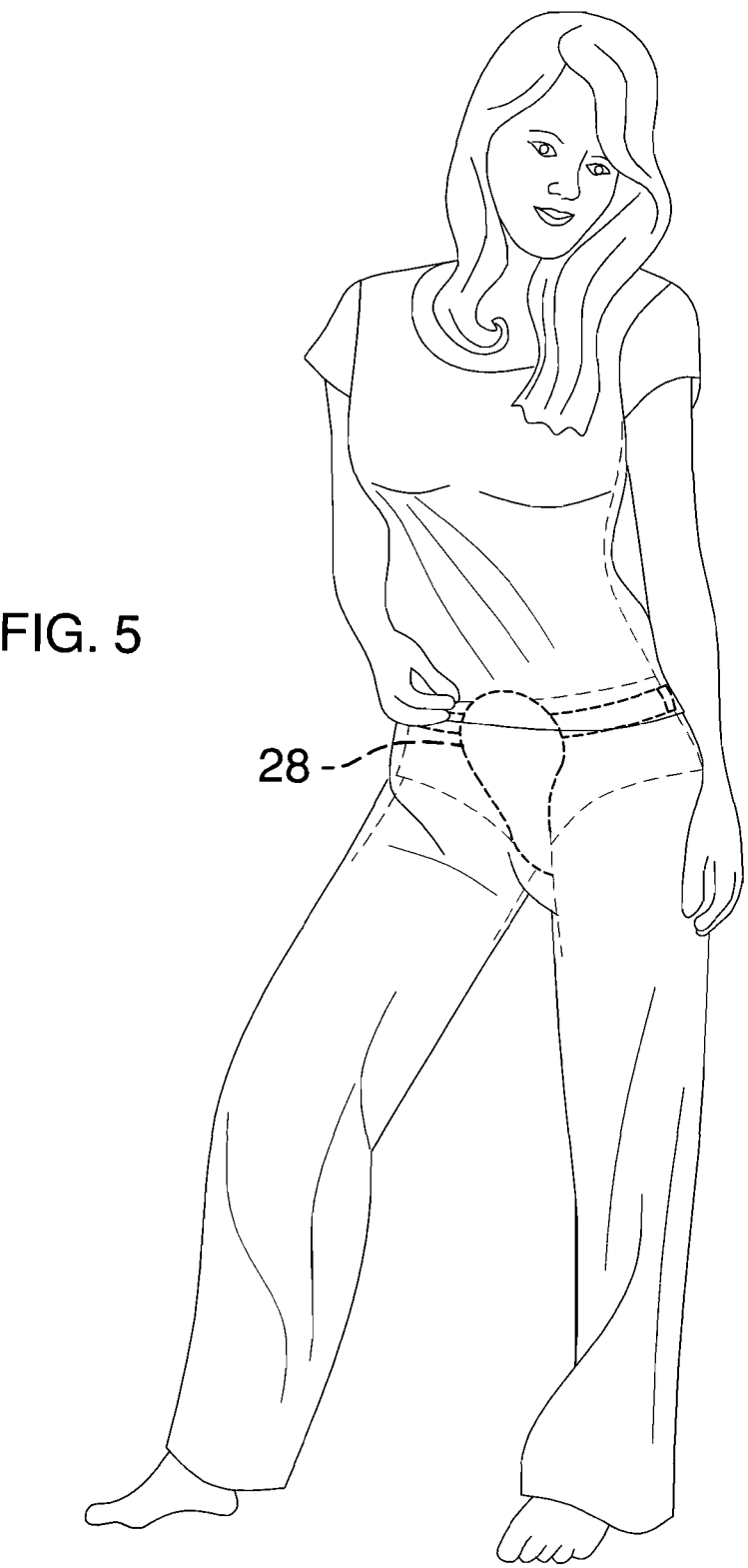
FIG. 5 is a perspective in-use view of an embodiment of the disclosure.

A first strap 40 has a first end 42 attached to the base member adjacent to the first edge 34 and a second end 44 to the base member 28 adjacent to the second edge 36. A second strap 46 has a first end 48 attached to the base member 28 adjacent to the first edge 34 and a second end 50 to the base member 28 adjacent to the second edge 36. The first 40 and second 46 straps are positioned on opposite sides of the base member 28 and are used to retain the base member 28 on a person as is shown in FIG. 5. The first 40 and second 46 straps each comprises a resiliently stretchable material. Each of the first 40 and second 48 straps has a break 52 therein so that each of the first 40 and second 48 straps includes a first strap section 54 and a second strap section 56. A pair of couplers 58 is provided. Each of the first 40 and second 46 straps has one of the couplers 58 attached thereto and releasably coupling together associated ones of the first 54 and second 56 strap sections. The couplers 58 may comprise hook and loop couplers.

In use, the pad 12 is placed against the body in a conventional manner and the first 40 and second 48 straps retain the pad 12 in place. The shape of the pad 12, as well as its size and in combination with the base member 28, inhibits leakage around the pad 12, particularly when the wearer of the pad 12 is lying in bed.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A feminine sanitary pad assembly configured to absorb menstrual flow, said assembly including:
   a panel being configured to absorb and retain fluids, said panel having a first end, a second end, a first lateral edge and a second lateral edge, said panel including a first end section including said first end, a second end section including said second end and a central section being attached to and extending between said first and second end sections, each of said first and second end sections having a circular shape, said first and second lateral edges of said central section being concavely arcuate;
   a base member being flexible and having an inner surface and an outer surface, said panel being non-removably attached to said inner surface, said base member having a first edge and a second edge positioned opposite of each other, said base member having a first end portion, a second end portion, and a central portion wherein said first end portion is coupled to said first end section of said panel, said second end portion is coupled to said second end section of said panel, and said central portion is coupled to said central section of said panel;
   a first strap having a first end attached to said base member adjacent to said first edge and a second end to said base member adjacent to said second edge; and
   a second strap having a first end attached to said base member adjacent to said first edge and a second end to said base member adjacent to said second edge, said first and second straps being positioned on opposite sides of said base member, said first ends of said first strap and said second strap extending outwardly substantially perpendicular to a longitudinal axis of the assembly from opposite lateral edges of said first end portion of said base member, said second ends of said first strap and said second strap extending outwardly substantially perpendicular to the longitudinal axis of the assembly from opposite lateral edges of said second end portion of said base member, said first and second straps being attached to said inner surface of said base member.

2. The assembly according to claim 1, wherein said panel has a length from said first end to said second end being greater than 20 cm.

3. The assembly according to claim 1, wherein said base member has a size and shape such that a peripheral flange is formed between said base member and said panel extending completely around said panel.

4. The assembly according to claim 3, wherein said base member is comprised of a cloth material.

5. The assembly according to claim 4, wherein said panel has a length from said first end to said second end being greater than 20 cm.

6. The assembly according to claim 1, wherein said first and second straps each comprise a resiliently stretchable material.

7. The assembly according to claim 6, further including:
   each of said first and second straps having a break therein such that each of said first and second straps includes a first strap section and a second strap section; and
   a pair of couplers, each of said first and second straps having one of said couplers attached thereto and releasably coupling together associated ones of said first and second strap sections.

8. The assembly according to claim 1, further including:
   each of said first and second straps having a break therein such that each of said first and second straps includes a first strap section and a second strap section; and
   a pair of couplers, each of said first and second straps having one of said couplers attached thereto and releasably coupling together associated ones of said first and second strap sections.

9. A feminine sanitary pad assembly configured to absorb menstrual flow, said assembly including:
   a panel being configured to absorb and retain fluids, said panel having a first end, a second end, a first lateral edge and a second lateral edge, said panel including a first end section including said first end, a second end section including said second end and a central section being attached to and extending between said first and second end sections, each of said first and second end sections having a circular shape, said first and second lateral edges of said central section being concavely arcuate, said panel having a length from said first end to said second end being greater than 20 cm;
   a base member being flexible and having an inner surface and an outer surface, said panel being non-removably attached to said inner surface, said base member having a first edge and a second edge positioned opposite of each other, said base member having a size and shape such that a peripheral flange is formed between said base member and said panel extending completely around said panel, said base member being comprised of a cloth material, said base member having a first end portion, a second end portion, and a central portion wherein said first end portion is coupled to said first end section of said panel, said second end portion is coupled to said second end section of said panel, and said central portion is coupled to said central section of said panel;
   a first strap having a first end attached to said base member adjacent to said first edge and a second end to said base member adjacent to said second edge;
   a second strap having a first end attached to said base member adjacent to said first edge and a second end to said base member adjacent to said second edge, said first and second straps being positioned on opposite sides of said base member, said first ends of said first strap and said second strap extending outwardly substantially perpendicular to a longitudinal axis of the assembly from opposite lateral edges of said first end portion of said base member, said second ends of said first strap and said second strap extending outwardly substantially perpendicular to the longitudinal axis of the assembly from opposite lateral edges of said second end portion of said base member, said first and second straps being attached to said inner surface of said base member;
   said first and second straps each comprising a resiliently stretchable material;
   each of said first and second straps having a break therein such that each of said first and second straps includes a first strap section and a second strap section; and
   a pair of couplers, each of said first and second straps having one of said couplers attached thereto and releasably coupling together associated ones of said first and second strap sections.

* * * * *